United States Patent
Fujino et al.

(10) Patent No.: US 11,491,170 B2
(45) Date of Patent: Nov. 8, 2022

(54) METHOD FOR MANUFACTURING FUNCTIONAL MATERIAL INCLUDING PLASMALOGEN

(71) Applicant: INSTITUTE OF RHEOLOGICAL FUNCTIONS OF FOOD, Fukuoka (JP)

(72) Inventors: Takehiko Fujino, Fukuoka (JP); Shiro Mawatari, Fukuoka (JP)

(73) Assignee: INSTITUTE OF RHEOLOGICAL FUNCTIONS OF FOOD, Fukuoka (JP)

( * ) Notice: Subject to any disclaimer, the term of this patent is extended or adjusted under 35 U.S.C. 154(b) by 304 days.

(21) Appl. No.: 16/622,473

(22) PCT Filed: Apr. 18, 2019

(86) PCT No.: PCT/JP2019/016670
§ 371 (c)(1),
(2) Date: Dec. 13, 2019

(87) PCT Pub. No.: WO2020/213132
PCT Pub. Date: Oct. 22, 2020

(65) Prior Publication Data
US 2021/0361681 A1    Nov. 25, 2021

(30) Foreign Application Priority Data
Apr. 18, 2019 (JP) .............................. JP2019-078994

(51) Int. Cl.
| | |
|---|---|
| *A61K 35/57* | (2015.01) |
| *A61K 31/685* | (2006.01) |
| *A61K 35/655* | (2015.01) |
| *A61P 29/00* | (2006.01) |
| *A61K 35/618* | (2015.01) |
| *C12P 13/00* | (2006.01) |

(52) U.S. Cl.
CPC ............ *A61K 31/685* (2013.01); *A61K 35/57* (2013.01); *A61K 35/618* (2013.01); *A61K 35/655* (2015.01); *A61P 29/00* (2018.01); *C12P 13/001* (2013.01)

(58) Field of Classification Search
None
See application file for complete search history.

(56) References Cited

U.S. PATENT DOCUMENTS

2013/0172293 A1    7/2013  Mawatari et al.

FOREIGN PATENT DOCUMENTS

| | | |
|---|---|---|
| JP | 2006-56803 | 3/2006 |
| JP | 2006-347937 | 12/2006 |
| JP | 2009-298729 | 12/2009 |
| JP | 2010-063406 | 3/2010 |
| JP | 2011115076 A * | 6/2011 |
| JP | 5483846 | 5/2014 |
| JP | 5489439 | 5/2014 |
| JP | 6518800 | 5/2019 |
| WO | 2012/039472 | 3/2012 |
| WO | 2017/109897 | 6/2017 |

OTHER PUBLICATIONS

Maeda et al. (2015) Advances in Clinical Chemistry, vol. 70, pp. 31-94. (Year: 2015).*
Yunoki et al. (2008) J. Am. Oil Chem. Soc. 85: 427-433. (Year: 2008).*
Masami Aoki, "Alzheimer's Disease, Sunsho Pharmaceutical for Alzheimer's Disease and Hoya's Improvement", Nihon Keizai Shimbun, Jan. 27, 2017, along with English translation.
International Search Report in International Patent Application No. PCT/JP2019/016670, dated Jul. 30, 2019.

* cited by examiner

*Primary Examiner* — Russell G Fiebig
(74) *Attorney, Agent, or Firm* — Greenblum & Bernstein, P.L.C.

(57) ABSTRACT

A method for manufacturing a functional material that contains plasmalogen, the method including treating an animal tissue containing plasmalogen with protease, and extracting the animal tissue treated with protease with an extraction liquid containing ethanol.

3 Claims, 2 Drawing Sheets

[Fig.1]

[Analysis conditions of phospholipids]

HPLC conditions

| | |
|---|---|
| LC system: | Agilent Technologies 1200 Series |
| Detector: | Agilent Technologies 1290 Infinity ELDS |
| Data: | Agilent OpenLAB |
| HPLC column: | Lichrosphere 100 Diol (250-3 mm, 5 um, MERCK MILLIPORE) |
| Guard column: | Lichrosphere 100 Diol (4-4 mm, 5 um, MERCK MILLIPORE) |
| Column temperature: | 50°C |
| Injection amount: | 10 μL |
| Sample solvent: | Hexane/Isopropanol (3:2, v/v) |
| Mobile phase A: | Hexane/Isopropanol/Acetic acid (85:14:1,v/v) + 0.08% triethylamine |

Concentration gradient:

| Time (min) | A (%) | B (%) |
|---|---|---|
| 0 | 96 | 4 |
| 21 | 63 | 37 |
| 25 | 15 | 85 |
| 26 | 15 | 85 |
| 29 | 96 | 4 |
| 34 | 96 | 4 |

ELSD conditions

| | |
|---|---|
| $N_2$ generator: | Airtech AT-5NP-CB |
| Evaporator temperature: | 60°C |
| Nebulizer temperature: | 30°C |
| $N_2$ gas flow rate: | 1.0 SLM |
| Data rate: | 80 Hz |
| Smoothing: | 4.5 sec. |
| PMT gain: | 6.0 |

[Fig.2]
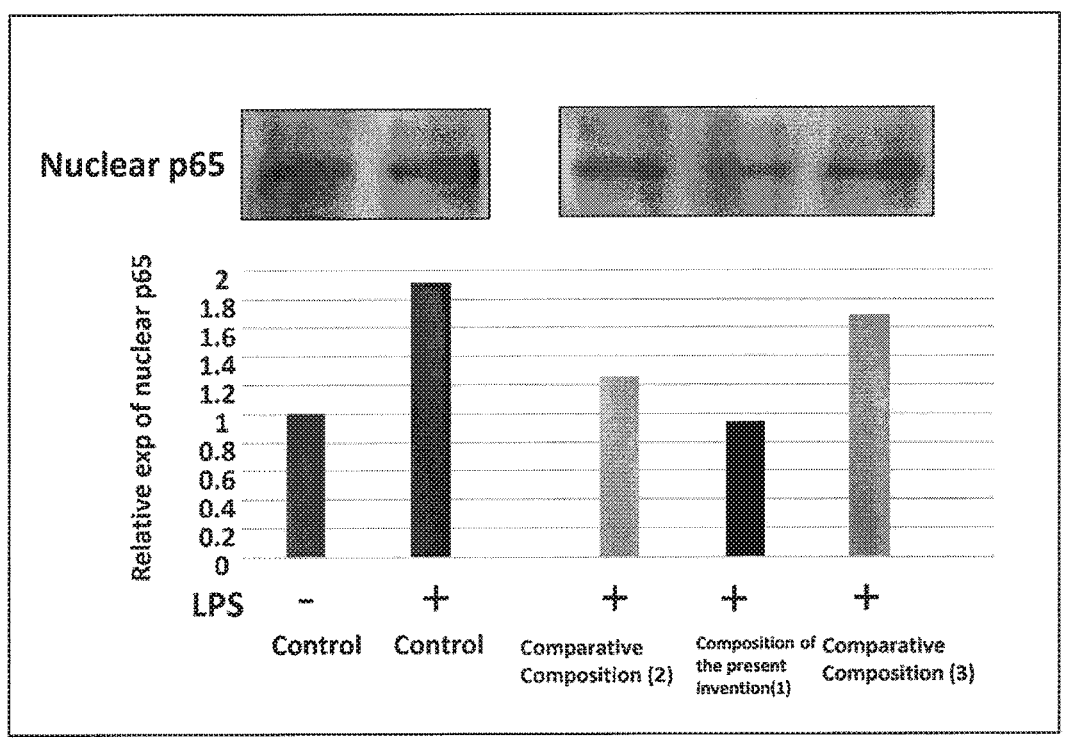

METHOD FOR MANUFACTURING FUNCTIONAL MATERIAL INCLUDING PLASMALOGEN

TECHNICAL FIELD

The present invention relates to a method for manufacturing functional material including plasmalogen.

BACKGROUND ART

Phospholipids are important as constituents of biological membrane. Among these, plasmalogen which is an ether phospholipid represents about 18% of phospholipids in biological membrane of mammals. This plasmalogen is known to be abundant particularly in cranial nerves, cardiac muscles, skeletal muscles, leukocytes, sperms, etc.

Since many plasmalogens are bound to polyunsaturated fatty acids such as docosahexaenoic acid and arachidonic acid, not only they work as reservoirs of secondary messengers of intercellular signals such as prostaglandin and leukotriene generated from these polyunsaturated fatty acids, they play an important role in cell fusion, and ion transport, etc.

Further, vinyl ether linkage (alkenyl linkage) of plasmalogen functions as antioxidation of cells since they are particularly sensitive to oxidative stress.

Further, plasmalogen is known for its action of promoting neurogenesis, action of suppressing nerve inflammation due to lipopolysaccharides (LPS), action of suppressing accumulation of amyloid β (Aβ) protein in brain, etc., and it is said to have effect on cranial nerve disorders such as Alzheimer's disease, Parkinson's disease, depression, and schizophrenia. Further, it is said to have effect for treating and ameliorating diabetes, metabolic syndrome, various infections, or immune disorders.

Conventionally, attempts have been made for extracting such plasmalogen from animal tissues (Patent references 1 and 2). For example, in Patent reference 1, proposed is a method comprising extracting and treating using ethanol as extracting solvent for breast meat of a layer chicken, and collecting the extraction liquid.

Further, in Patent Document 2, proposed is a method comprising performing ethanol extraction treatment to animal tissue to obtain an ethanol extract, treating the ethanol extract with phospholipase A1 (PLA1), hydrolyzing diacyl-type glycerophospholipid, further treating with water soluble ketone-based solvent, collecting insoluble parts, performing solvent distribution of the insoluble parts with a mixed organic solvent of aliphatic hydrocarbon solvent, and water-soluble ketone solvent and water, and collecting the mixed organic solvent part.

PRIOR ART REFERENCES

Patent References

[Patent reference 1] Japan Patent No. 5483846
[Patent reference 2] Japan Patent No. 5489439

SUMMARY OF THE INVENTION

Object to be Solved by the Invention

As it is stated in the above, though attempts are made to obtain useful plasmalogen from animal tissues, it cannot be said that plasmalogen is efficiently obtained.

The object of the present invention is to provide a method for efficiently obtaining plasmalogen from animal tissues.

Means to Solve the Object

The present inventors made a keen study to efficiently extract plasmalogen from animal tissues, and as a result, they found out that by treating animal tissues with protease, and then extracting with ethanol, a large amount of plasmalogen can be extracted. The present invention has been thus completed. Further, they found out that functional materials obtained by such method are significantly effective for suppressing cranial nerve inflammation.

Specifically, the present invention is as follows.

[1] A method for manufacturing a functional material comprising plasmalogen, the method comprising an enzyme treatment step of treating an animal tissue comprising plasmalogen with protease, and an extraction step of extracting the animal tissue treated with protease with an extraction liquid comprising ethanol;

[2] The method for manufacturing a functional material comprising plasmalogen according to [1], wherein the animal tissue is a tissue of an animal selected from scallops, sea squirt, and birds;

[3] The method for manufacturing a functional material comprising plasmalogen according to [1] or [2], wherein the protease is a neutral protease;

[4] A method for manufacturing a composition for suppressing cranial nerve inflammation, comprising mixing a functional material obtained by the manufacturing method according to any one of [1] to [3];

[5] A functional material obtainable from the manufacturing method according to any one of [1] to [3];

[6] A composition for suppressing cranial nerve inflammation obtainable from the manufacturing method according to [4];

[7] The composition for suppressing cranial nerve inflammation according to [6], for preventing or ameliorating a cranial nerve disease selected from the group consisting of dementia, Parkinson's disease, depression, and schizophrenia.

Effect of the Invention

According to the present invention, plasmalogen can be efficiently extracted from animal tissues.

BRIEF EXPLANATION OF DRAWINGS

FIG. 1 It is a figure showing analysis conditions of phospholipids in the Examples.

FIG. 2 It is a figure showing the effect of suppressing inflammation of the composition of the present invention, prepared in the Example for LPS induced inflammation signal in mouse-derived microglial cells (MG6 and BV2).

MODE FOR PRACTICING THE INVENTION

The method for manufacturing a functional material comprising plasmalogen of the present invention is characterized by comprising an enzyme treatment step of treating an animal tissue comprising plasmalogen with protease, and an extraction step of extracting the animal tissue treated with protease with an extraction liquid comprising ethanol. The manufacturing method of the present invention can comprise another step before or after the enzyme treatment step and the extraction step. However, to provide a step of treating with a lipolytic enzyme before the extraction step (particularly at the same time as treating with protease, or after the treatment) may decrease the effect of suppressing cranial nerve inflammation, it is preferred that there is no step of treating with a lipolytic enzyme in view of this point.

[Enzyme Treatment Step]

The enzyme treatment step is a step of treating animal tissues comprising plasmalogen with protease.

The animal tissue is not particularly limited as long as it is an animal tissue comprising plasmalogen, and examples include aquatic animals such as scallops, sea squirt, sea cucumber, abalone, salmon, skipper and bonito, and birds. Among these, scallops, sea squirt, and birds are preferred, and as parts to be used, a part to eat (edible part) is preferred.

Scallops in the present invention refer to edible clam belonging to Pectinidae, and for example, those belonging to the genus *Mizuhopecten*, and the genus *Pecten* can be exemplified. Specifically, common scallop (scientific name: *Mizuhopecten yessoensis*) collected in Japan, or European scallop (scientific name: *Pecten maximus* (Linnaeus)) collected in Europe can be exemplified. As edible parts, scallop eye and taenia can be exemplified.

Sea squirts in the present invention refer to edible chordates belonging to Pyuridaethe, and those belonging to the genus *Haloncynthia*, the genus *Halocynthia* aurantium can be exemplified. Specifically, Maboya (scientific name: *Haloncynthia roretzi*) and Akaboya (scientific name: *Halocynthia aurantium*) can be exemplified. As edible parts, meats (fascia) can be exemplified.

Birds in the present invention are not particularly limited as long as it is edible birds, and for example, chicken, silky fowl and canard can be exemplified. As edible parts, breast meat comprising plasmalogen in abundance can be exemplified.

These animal tissues can be cut products, but it is preferred to use ground products since plasmalogen can be extracted more efficiently.

As protease used in the enzyme treatment, protease from filamentous bacterium of the genus *Aspergillus*, and the genus *Rhizopus*, etc.; protease from the bacterium of the genus *Bacillus*, etc.; and protease extracted from plants such as papaya and pineapple can be exemplified, and commercially available protease agent can be used. Among these, protease from filamentous bacterium is preferred and protease from *aspergillus* is particularly preferred. Further, since plasmalogen is not stable when acidic or basic, it is preferred to perform enzyme treatment in an environment of about pH 4 to 10, and at least it is preferred to use an enzyme comprising neutral protease.

As used amount of protease, it is preferably for example about 0.1-10.0 g, more preferably about 0.2-8.0 g, and further preferably about 0.3-5.0 g with respect to 100 g of animal tissues.

[Extraction Step]

In the extraction step, animal tissues treated with protease are extracted with an extraction liquid comprising ethanol.

As extraction liquid comprising ethanol used in the extraction step can be a water-containing ethanol, and it can also be a mixture of ethanol and another organic solvent. The ethanol concentration is preferably 50 mass % or more, more preferably 80 mass % or more, and further preferably 95 mass % or more. It is particularly preferable to be substantially 100 mass %.

As used amount of ethanol, it is preferably for example about 100-300 mL, more preferably about 200-2000 mL, and further preferably about 250-1000 mL with respect to 100 g of animal tissues. Extraction using ethanol can be performed plural times.

After performing the extraction treatment, by removing a solid part and collecting an extraction liquid, and by drying hard according to need, a functional material comprising plasmalogen of the present invention can be obtained.

Further, a concentration treatment for increasing plasmalogen concentration can be performed to the ethanol extract. For example, after the ethanol extraction step, a lipophilic solvent extraction step for extracting with an extraction liquid comprising a lipophilic solvent can be provided. As lipophilic solvent, for example, aliphatic hydrocarbon and aromatic hydrocarbon can be exemplified, and hexane, isopropanol, or a mixture of these are particularly preferred.

As for the amount of plasmalogen contained in a functional material obtained by the manufacturing method of the present invention, it is preferably 0.001-100 mg/g (converted to wet weight), and more preferably 0.1-10 mg/g.

The functional material comprising plasmalogen of the present invention can be used by being contained in foods, medicines, cosmetics, etc. As foods, general foods, as well as foods for specified health use, dietary supplements, functional foods, and supplements can be exemplified. As cosmetics, milk lotion, cream, lotion, oil, facial masks, facial wash, cleansing, and body wash can be exemplified.

Since the functional material of the present invention contains a large amount of plasmalogen, and is particularly effective for suppressing cranial nerve inflammation, foods comprising the functional material of the present invention, etc. can be a composition for suppressing cranial nerve inflammation. It is particularly useful for preventing or ameliorating cranial nerve lesions including dementia such as Alzheimer's disease, Parkinson's disease, melancholia, and schizophrenia. Further, foods comprising the functional material of the present invention, etc. are effective for ameliorating atomic dermatitis, suppressing hyperglycemia, decreasing blood cholesterol, promoting metabolism of lipids, anti-fatigue, maintaining level of albumin in the blood, recovering liver function, suppressing decrease of muscle during exercise, ameliorating insomnia, etc. Further, cosmetics comprising the functional material of the present invention are effective for preventing skin aging intending ameliorating wrinkles or whitening.

The form of foods, medicines, cosmetics, etc. is not particularly limited, and for example, a form of tablet, capsule, powder, granule, liquid, grain, bar, plate, block, solid, circle, paste, cream, caplet, gel, chewable, and stick can be exemplified.

Example 1

By the following procedures, a composition comprising plasmalogen was extracted from each material (edible parts of scallops, edible parts of birds, edible parts of sea squirt) and analyzed. Specifically, as scallops, taenia of common scallop (scientific name: *Mizuhopecten yessoensis*) was used. As birds, breast meat of chicken was used. As sea squirt, meats (fascia) of Maboya (scientific name: *Halocynthia roretzi*) was used.

1. 50 g of material (scallop, chicken breast meat, sea squirt) was thawed, and cut to pieces with scissors.
2. The following test solutions were prepared.
   a) only 50 mL of 0.1 M citric acid solution (pH 4.5)
   b) 50 mL of 0.1 M citric acid solution (pH 4.5)+0.25 g of Kokulase (registered trademark) •P grain (source: *Aspergillus oryzae*) (manufactured by Mitsubishi-Chemical Foods Corporation)
   c) 50 mL of 10 mM Tris-HCl Buffer (pH 7.4)+0.25 g of Protease P "Amano" 3SD (source: genus *Aspergillus*) [manufactured by Amano Enzyme Inc.]
   d) 50 mL of 10 mM Tris-HCl Buffer (pH 7.4)+1.25 g of protein SD-NY10 (source: genus *Bacillus*) [manufactured by Amano Enzyme Inc.]
3. The material and each of the above test solutions a) to d) were mixed, and pulverized with a blender (HGBSS, manufactured by WARING) (10 sec.×3 times).
4. The mixture was reacted at 50° C. for 60 minutes (stirred with a glass rod once about every 15 minutes).
5. 250 mL of ethanol was added, and the mixture was pulverized in a blender (10 sec.×2 times).
6. The resultant was left for 30 minutes (stirred with a glass rod for 10 rotations about every 5 minutes).
7. Suction filtration was performed to collect the filtrate.
8. 1 mL of the filtrate was taken in a Spitz tube, and used for phospholipid analysis.
9. The remaining filtrate was dried hard with an evaporator, and the total lipid weight was measured.

The results of each analysis are shown in the following.
(1) Total Lipid Weight

The total lipid weights (g per 50 g of material) of the extract using the above-mentioned test solutions (a)-(d) are shown in Table 1.

TABLE 1

| g per 50 g of material | Scallop | Chicken breast meat | Sea squirt |
| --- | --- | --- | --- |
| a) no protease | 3.76 | 2.49 | 4.28 |
| b) Kokulase P | 5.52 | 4.54 | 5.95 |
| c) Protease-Amano 3SD | 5.95 | 4.69 | 6.23 |
| d) Protin SD-NY10 | 6.35 | 5.61 | 6.74 |

(2) The proportions (HPLC surface level) of plasmalogens (pl-PE+pl-PC) in the analysis conditions of phospholipid (see FIG. 1) are shown in Table 2.

TABLE 2

| | Scallop | Chicken breast meat | Sea squirt |
| --- | --- | --- | --- |
| a) no protease | 47.3 | 21.8 | 40.8 |
| b) Kokulase P | 52.1 | 22.9 | 42.0 |
| c) Protease-Amano 3SD | 48.6 | 21.0 | 39.4 |
| d) Protin SD-NY10 | 48.3 | 19.8 | 42.9 |

(3) Increase rate of plasmalogens (pl-PE+pl-PC) by protease treatment

The total lipid weight obtained in the above (1) was multiplied by the proportion of plasmalogens (pl-PE+pl-PC) obtained in the above (2), and by using "(a) no protease" as a standard (1.0), the amounts of plasmalogens (pl-PE+pl-PC) were compared. The results are shown in Table 3.

The proportion of phospholipid in the entire total lipid did almost not change even by performing a protease treatment.

TABLE 3

| | Scallop | Chicken breast meat | Sea squirt |
| --- | --- | --- | --- |
| a) no protease | 1.0 | 1.0 | 1.0 |
| b) Kokulase P | 1.6 | 1.9 | 1.4 |
| c) Protease-Amano 3SD | 1.6 | 1.8 | 1.4 |
| d) Protin SD-NY10 | 1.7 | 2.0 | 1.7 |

As shown in Table 3, it can be seen that by performing a protease treatment, the extraction amount of plasmalogen significantly increases.

Example 2

[Preparation of Scallop Extract 1]

By the following procedures, a functional material of the present invention (composition of the present invention) was obtained from common scallop (scientific name: *Muzuhopecten yessoensis*)
1. 200 g of material (raw scallop) was thawed, and cut to pieces with scissors.
2. 1.0 g of Kokulase (registered trademark) •P grain (source: *Aspergillus oryzae*) (manufactured by Mitsubishi-Chemical Foods Corporation) was added.
3. The mixture was pulverized with a blender (10 sec.×2 times).
4. By using a stirrer, the resultant was reacted at 50° C. for 30 minutes.
5. 800 ml of ethanol was added.
6. The mixture was pulverized with a blender (10 sec.×2 times).
7. The mixture was stirred at 50° C. for 20 minutes.
8. Suction filtration was performed.
9. The filtrate was dried hard with a rotary evaporator.
10. 500 mL of hexane/isopropanol (3:2) was added and mixed.
11. 250 mL of water was added and mixed.
12. The resultant was placed in a separating funnel, and mixed well.
13. The resultant was left to stand for 10 minutes.
14. The lower layer (aqueous layer) was taken, and dried hard with $N_2$ gas.
   The composition (amino acid+other water soluble components) obtained in this step was used as comparative composition (3).
15. The upper layer (hexane layer) was taken, and dried hard with $N_2$ gas.
   The composition (pl-PE+other lipids) obtained in this step was used as the composition of the present invention (1).

[Preparation of Scallop Extract 2 (a Case Using Protease and Phospholipase, and not Performing Ethanol Extraction (Comparative Example))]
1. 50 mL of 0.1 M citric acid (pH 4.5) was added with 0.5 g of Kokulase P and 0.8 g of phospholipase A1 (PLA1), and mixed.
2. 200 g of material (raw scallop) was thawed, and cut to pieces with scissors.
3. 1. was added and pulverized with a blender (10 sec.×3 times)
4. The resultant was reacted at 50° C. for 1 hour (mixed with a glass rod once every 15 minutes).
5. 1000 mL of hexane/isopropanol (3:2) was added.
6. The mixture was stirred at room temperature for 10 minutes.
7. The supernatant was subjected to suction filtration.

8. The resultant was washed with 200 mL of hexane/isopropanol (3:2), and again subjected to suction filtration.
9. The filtrate was placed in a separating funnel.
10. 800 mL of aqueous solution of sodium sulfate was added, and mixed well.
11. The mixture was left to stand.
12. The lower layer was discarded.
13. The upper layer was dried hard with a rotary evaporator.
14. 4 mL of hexane was added, well suspended by ultrasound, and place in a spin down tube.
15. 40 mL of acetone (4° C.) was added and mixed.
16. The resultant was left at −30° C. for 1 hour to overnight.
17. The resultant was centrifuged at 3000 rpm, 10 min, at 4° C.
18. The supernatant was discarded and the precipitate was collected.
19. The resultant was dried overnight with a desiccator.

The composition (pl-PE+pl-PC+CAEP+Cholesterol) obtained in this step was used as comparative composition (2). pl-PC is a choline plasmalogen, and CAEP is a ceramide aminoethyl phosphonic acid.

[Confirmation of the Action of Suppressing Inflammation of the Composition of the Present Invention]

At the time of inflammation, mainly in microglia cells, p65 protein which is a subunit of inflammation factor NF-kB migrates into nucleus, and induces inflammatory cytokines such as IL-1beta and TNF-alpha. Lipopolysaccharides (LPS) increase p65 expression in nucleus to induce inflammatory signals. In the present Example, the effect of the composition of the present invention on LPS induced inflammatory signal in mouse-derived microglia cells (MG6 and BV2) are studied.

Specific protocols are as follows.
1. The compositions (1)-(3) were dissolved in water.
2. Mouse-derived microglia cells (MG6 and BV2) were cultured overnight in a 2% serum DMEM medium added or not added with the composition. For the medium added with the composition, it was adjusted such that an equivalent amount (5 μg/mL) of active plasmalogen is contained, respectively.
3. Then, LPS (1 μg/ml) was added, and treated for 6 hours. The subjects of assessment were the five types, LPS not added "control LPS-", LPS added "control LPS+", "composition of the present invention (1) LPS+", "comparative composition (2) LPS+", and "comparative composition (3) LPS*".
4. 6 hours later, nucleus was extracted by cell collection and cell fractionation.
5. By using the nucleus extract, western blot was performed, and p65 which is the inflammatory marker was detected.
6. By confirming this protein expression, it was tested whether the compositions (1)-(3) decrease LPS induced inflammatory signal (p65 expression in nucleus) in microglia cells.

The results are shown in FIG. 2.

As it is shown in FIG. 2, the composition of the present invention (1) and comparative example (2) significantly suppressed inflammation induced by lipopolysaccharide (LPS), and the suppression effect was superior in the composition of the present invention (1) than in the comparative composition (2).

INDUSTRIAL APPLICABILITY

The functional material comprising plasmalogen manufactured by the manufacturing method of the present invention can be used in foods or cosmetics, and thus is industrially useful.

The invention claimed is:

1. A method for manufacturing a functional material comprising plasmalogen, the method comprising:
treating an animal tissue comprising plasmalogen with protease; and
extracting the animal tissue treated with protease with an extraction liquid comprising ethanol, and
wherein no treating with a lipolytic enzyme is performed at the same time or after treating with protease.

2. The method for manufacturing a functional material comprising plasmalogen according to claim 1, wherein the animal tissue is a tissue of an animal selected from scallops and sea squirt.

3. The method for manufacturing a functional material comprising plasmalogen according to claim 1, wherein the protease is a neutral protease.

* * * * *